US012667251B2

(12) United States Patent　　　(10) Patent No.:　US 12,667,251 B2
Tanaka　　　　　　　　　　　　　　(45) Date of Patent:　　Jun. 30, 2026

(54) LINEAR MOTOR AND MEDICAL CARE APPARATUS INCLUDING THE SAME

(71) Applicant: J. MORITA MFG. CORP., Kyoto (JP)

(72) Inventor: Tsuyoshi Tanaka, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 281 days.

(21) Appl. No.: 18/643,564

(22) Filed: Apr. 23, 2024

(65) Prior Publication Data

US 2024/0349998 A1　　Oct. 24, 2024

(30) Foreign Application Priority Data

Apr. 24, 2023　(JP) ................................. 2023-070881

(51) Int. Cl.
*A61B 1/24*　　　(2006.01)
*A61B 1/00*　　　(2006.01)

(52) U.S. Cl.
CPC ............ *A61B 1/24* (2013.01); *A61B 1/00045* (2013.01); *A61B 1/00154* (2013.01); *A61B 1/00158* (2013.01)

(58) Field of Classification Search
CPC . Y02P 40/10; A61B 1/00045; A61B 1/00154; A61B 1/00158; A61B 1/24; H02K 33/16; H02K 41/031
See application file for complete search history.

(56) References Cited

U.S. PATENT DOCUMENTS

| | | | | |
|---|---|---|---|---|
| 2019/0293414 A1* | 9/2019 | Sorimoto | ................. | G01B 9/02 |
| 2020/0069169 A1* | 3/2020 | Tanaka | ............... | A61B 1/00194 |
| 2023/0301757 A1* | 9/2023 | Kaji | ..................... | A61C 9/0053 |

FOREIGN PATENT DOCUMENTS

| | | | |
|---|---|---|---|
| JP | 4-6281 U | | 1/1992 |
| JP | 2006-220776 A | | 8/2006 |
| JP | 2020-34487 A | | 3/2020 |
| JP | 2020034487 A | * | 3/2020 |

(Continued)

OTHER PUBLICATIONS

JP-2020034487-A, all pages (Year: 2020).*

(Continued)

*Primary Examiner* — Naishadh N Desai
(74) *Attorney, Agent, or Firm* — Oblon, McClelland, Maier & Neustadt, L.L.P.

(57)　　　　　ABSTRACT
The present disclosure provides a linear motor that undergoes no deterioration of the measurement accuracy or the driving accuracy depending on a driving situation, and a medical care apparatus including the linear motor. The linear motor of the present disclosure is a linear motor that moves linearly, the linear motor including: a movable element including a permanent magnet; a stator including a coil positioned to face the permanent magnet; and two parallel linear guides configured to guide the movable element to move linearly. Support portions provided on the linear guides, respectively, and holding portions provided on the movable element to correspond to the support portions are fitted with play and thereby the movable element is attached to the linear guides. A position where the permanent magnet is attached to the movable element is asymmetrical with respect to each of the holding portions.

20 Claims, 9 Drawing Sheets

(56) References Cited

FOREIGN PATENT DOCUMENTS

JP          6883559 B2      6/2021

OTHER PUBLICATIONS

Extended European Search Report issued Oct. 1, 2024 in European Patent Application No. 24168752.4, 9 pages.
Japanese Notice of Reasons for Refusal issued Aug. 5, 2025 in Japanese Patent Application No. 2023-070881 (with English Translation), 4 pages.

* cited by examiner

FIG.3

LINEAR MOTOR AND MEDICAL CARE APPARATUS INCLUDING THE SAME

CROSS REFERENCE TO RELATED APPLICATIONS

This nonprovisional application is based on Japanese Patent Application No. 2023-070881 filed on Apr. 24, 2023 with the Japan Patent Office, the entire contents of which are hereby incorporated by reference.

BACKGROUND

Technical Field

The present disclosure relates to a linear motor and a medical care apparatus including the same.

Description of the Background Art

Conventionally, a three-dimensional scanner has been known as a medical care apparatus that scans a tooth and a surrounding soft tissue in an oral cavity and obtains three-dimensional shape data. For example, Japanese Patent No. 6883559 discloses a scanner in which a lens and a counterweight are moved linearly by a linear motor.

SUMMARY

In the three-dimensional scanner disclosed in Japanese Patent No. 6883559, a plurality of support portions provided on the object side and holding portions provided on the plurality-of-linear-guides side, respectively, are fitted with play, which makes it possible to linearly move the lens and the counterweight by the linear motor while minimizing an influence of assembly errors of the apparatus, and obtain three-dimensional shape data of a tooth and a surrounding soft tissue in an oral cavity. However, since the support portions and the holding portions are fitted with play, the lens may sometimes be inclined with respect to the support portions and this inclination may sometimes vary depending on a driving situation of the linear motor. Therefore, even if calibration is performed and measurement is started when the lens has a certain inclination, the measurement accuracy may deteriorate because the inclination of the lens varies depending on the driving situation of the linear motor. In addition, in a medical care apparatus in which a cutting tool or the like is driven by a linear motor, the driving accuracy may deteriorate.

The present disclosure has been made to solve the above-described problem and an object thereof is to provide a linear motor that undergoes no deterioration of the measurement accuracy or the driving accuracy depending on a driving situation, and a medical care apparatus including the linear motor.

A linear motor according to the present disclosure is a linear motor that moves linearly, the linear motor including: a movable element including a permanent magnet; a stator including a coil positioned to face the permanent magnet; and two parallel linear guides configured to guide the movable element to move linearly. Support portions provided on the linear guides, respectively, and holding portions provided on the movable element to correspond to the support portions are fitted with play and thereby the movable element is attached to the linear guides. A position where the permanent magnet is attached to the movable element is asymmetrical with respect to each of the holding portions.

A medical care apparatus according to the present disclosure includes: the linear motor described above; and a housing configured to hold the linear motor such that the movable element can move linearly along the linear guides.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 3 is a diagram for illustrating a positional relationship between a lens and a counterweight in the three-dimensional scanner according to the embodiment.

DETAILED DESCRIPTION

An embodiment of the present disclosure will be described hereinafter with reference to the drawings.

Embodiment

First, a configuration of a medical care apparatus according to an embodiment of the present disclosure will be described. In the embodiment, a three-dimensional scanner that can be used for dental care will be described as one example of the medical care apparatus. The three-dimensional scanner is an intra oral scanner for obtaining a three-dimensional shape of a tooth in an oral cavity. The three-dimensional scanner according to the embodiment is not limited to the intra oral scanner, but is also applicable to any three-dimensional scanner having a similar configuration. For example, the three-dimensional scanner according to the embodiment is also applicable to a scanner that takes an image of the inside of a human ear, in addition to the inside of an oral cavity, and obtains a three-dimensional shape of the inside of an outer ear. In addition, the medical care apparatus is not limited to the three-dimensional scanner, but is also applicable to a medical care apparatus in which a cutting tool is driven.

In addition, the medical care apparatus according to the embodiment is applicable not only to a dental care but also to any type of medical cares in the fields of ophthalmology, otolaryngology, radiology, internal medicine, surgery, veterinary science, and the like. Also, the medical care includes a diagnosis and a treatment.

[Configuration of Three-Dimensional Scanner]

Figure 1:
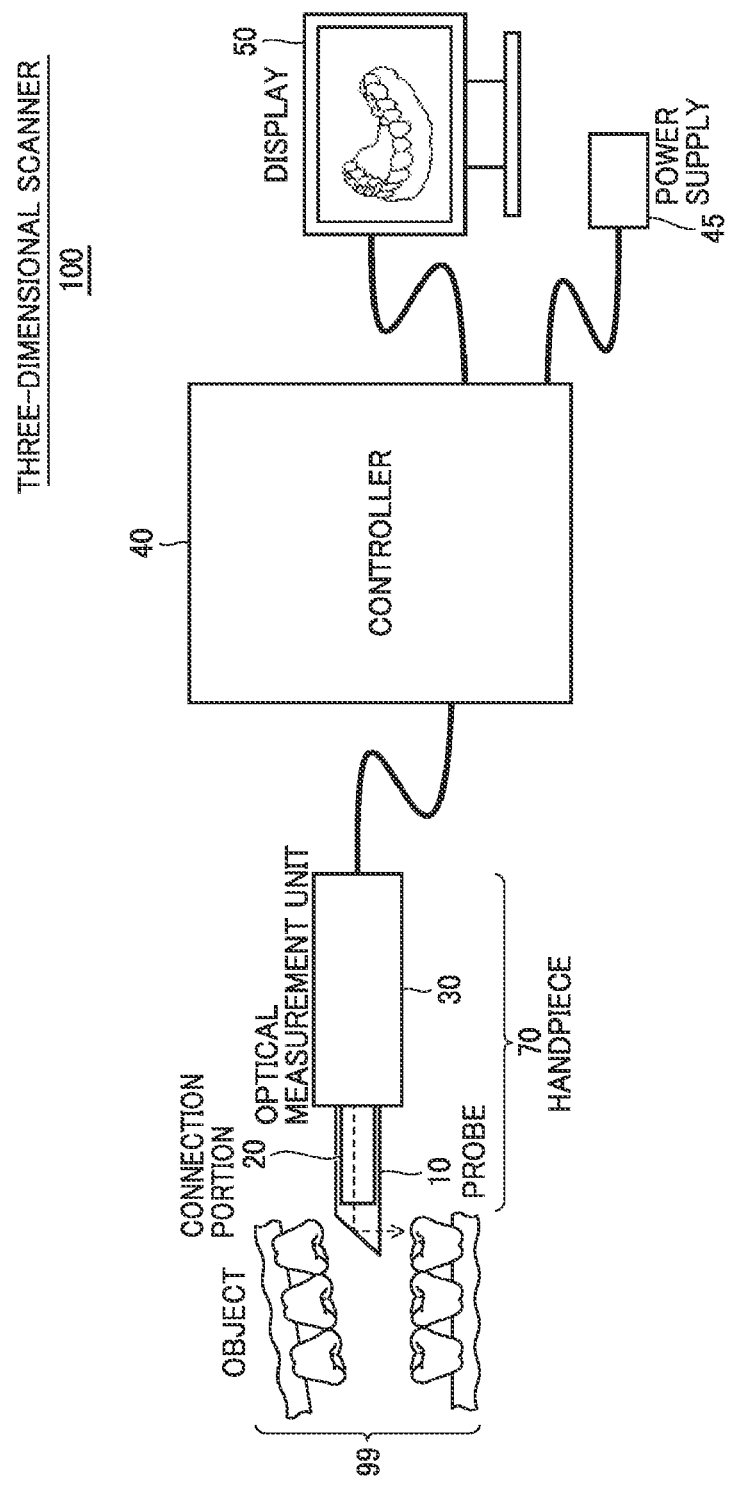
FIG. 1 is a schematic diagram showing a configuration of a three-dimensional scanner according to an embodiment.

FIG. 1 is a schematic diagram showing a configuration of a three-dimensional scanner 100 according to an embodiment. Three-dimensional scanner 100 corresponds to one example of "medical care apparatus". As shown in FIG. 1, three-dimensional scanner 100 includes a handpiece 70, a controller 40, a display 50, and a power supply 45. Handpiece 70 is a hand-held member and includes a probe 10, a connection portion 20 and an optical measurement unit 30.

Probe 10 is inserted into an oral cavity and projects light having a pattern (hereinafter also simply referred to as "pattern") onto an object 99 such as a tooth. Probe 10 guides reflected light from object 99 having the pattern projected thereon to optical measurement unit 30. Probe 10 is removably mounted on connection portion 20 to cover an outer perimeter of a tip portion of connection portion 20. Therefore, an operator can remove only probe 10 that may come into contact with a living body from optical measurement unit 30 and perform sterilization treatment (e.g., autoclave treatment under a high-temperature and high-humidity environment) on probe 10 as infection countermeasures.

Connection portion 20 is a part of optical measurement unit 30, protrudes from optical measurement unit 30, and has a shape that can be fitted to the root of probe 10. Connection portion 20 includes an optical component such as a lens system for guiding the light taken in by probe 10 to optical measurement unit 30, a cover glass, an optical filter, and a phase difference plate (¼ wavelength plate).

Optical measurement unit 30 projects the pattern onto object 99 through probe 10 and takes an image of the projected pattern. Although optical measurement unit 30 according to the embodiment is configured to obtain a three-dimensional shape using the principle of a focusing method as described below, optical measurement unit 30 according to the embodiment may be configured to obtain a three-dimensional shape using the principle such as the focusing method, a triangular method or a confocal method. In other words, optical measurement unit 30 may use any principle, as long as optical measurement unit 30 includes a configuration that changes a focal position of a projection pattern and an optical sensor and optical measurement unit 30 is configured to obtain a three-dimensional shape using an optical method.

Controller 40 controls the operation of optical measurement unit 30, and processes the image taken by optical measurement unit 30 and obtains a three-dimensional shape. Although not shown, controller 40 includes a central processing unit (CPU) serving as a control center, a read only memory (ROM) that stores a program, control data and the like for the operation of the CPU, a random access memory (RAM) that functions as a work area of the CPU, and an input/output interface for maintaining the signal integrity with a peripheral device. Controller 40 can also output the obtained three-dimensional shape to display 50, and can also input information such as setting of optical measurement unit 30 through a not-shown input device or the like.

At least a part of arithmetic operations for processing the taken image and obtaining the three-dimensional shape may be implemented as software by the CPU of controller 40, or may be implemented as hardware that performs processing separately from the CPU. At least a part of the processing unit such as the CPU or the hardware may be incorporated into optical measurement unit 30. Although FIG. 1 depicts each component (30, 40, 45, 50) of three-dimensional scanner 100 as being connected by a cable (a thick line in the figure), a part or the whole of the connection may be implemented by wireless communication. When controller 40 is small-sized and lightweight enough to lift controller 40 with one hand, controller 40 may be provided in handpiece 70.

Display 50 shows a measurement result of a three-dimensional shape of object 99 obtained by controller 40. Display 50 can also show other information such as setting information of optical measurement unit 30, patient information, an activation state of the scanner, a manual, and a help screen. A stationary liquid crystal display, a head-mounted display, a glass-type wearable display or the like is, for example, applicable as display 50. In one embodiment, a plurality of displays 50 may be provided and the measurement result of the three-dimensional shape and the other information may be shown on the plurality of displays 50 simultaneously or in a divided manner.

Power supply 45 supplies electric power to optical measurement unit 30 and controller 40. Although power supply 45 may be provided outside controller 40 as shown in FIG. 1, power supply 45 may be provided inside controller 40 or inside handpiece 70. In one embodiment, a plurality of power supplies 45 may be provided such that electric power can be supplied to controller 40, optical measurement unit 30 and display 50 individually.

[Configuration of Handpiece]

Figure 2A:
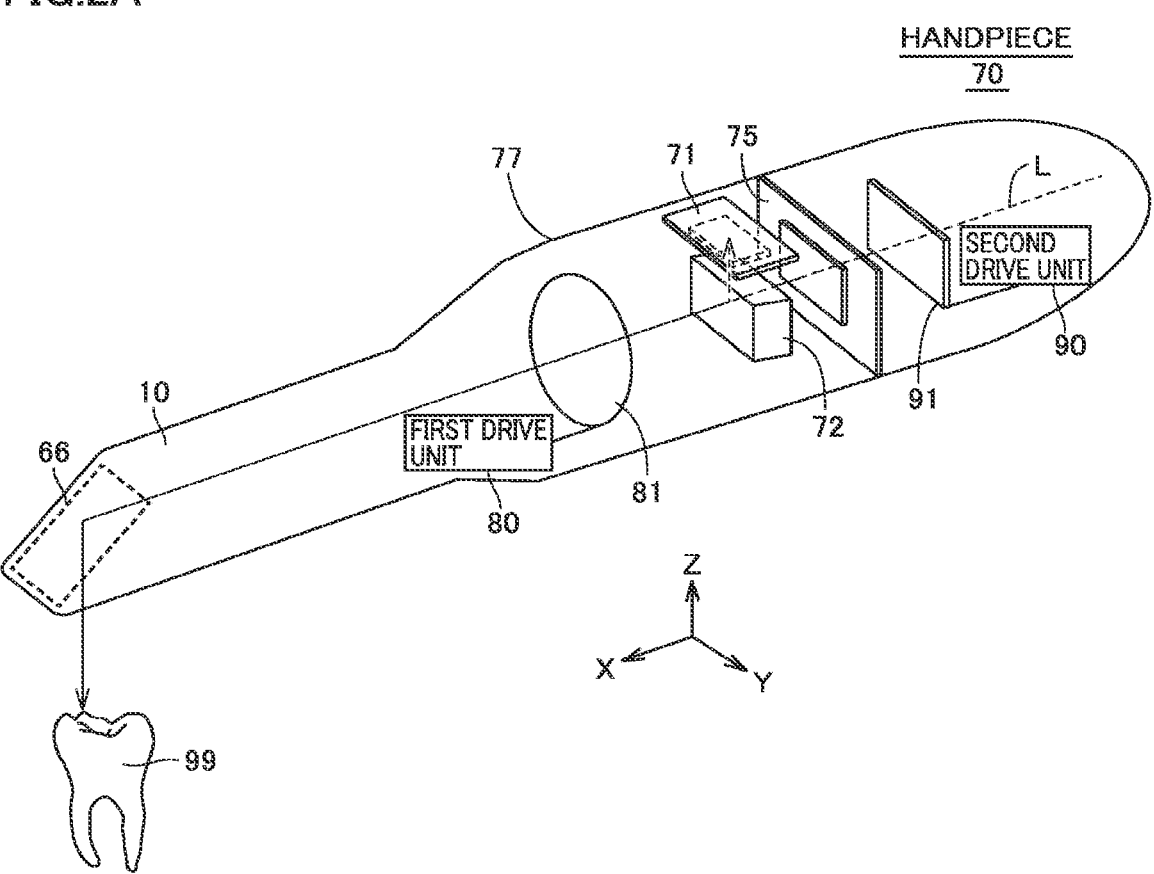
FIG. 2A is a schematic diagram showing a configuration of a handpiece according to the embodiment.
Figure 2B:
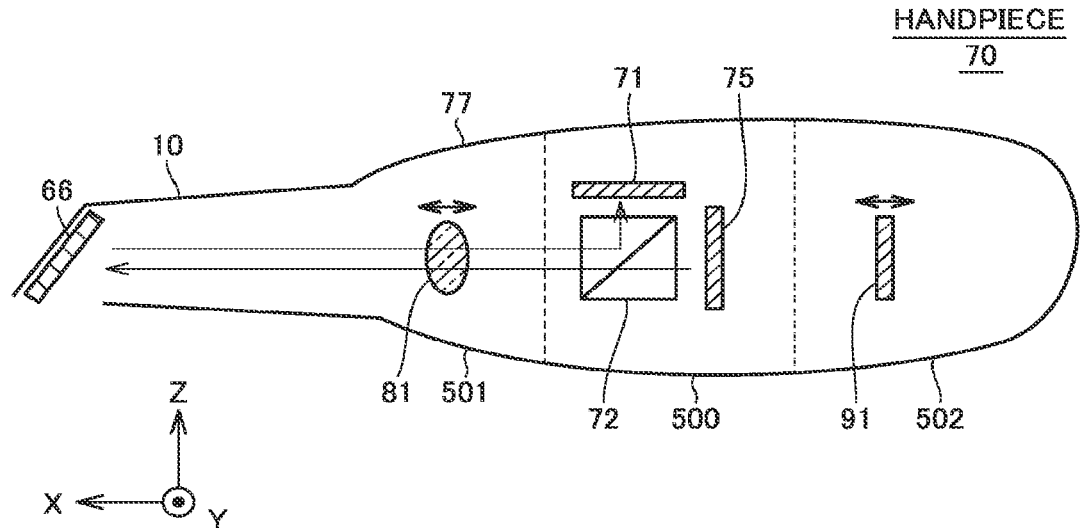
FIG. 2B is a schematic diagram showing an X-Z cross section of the handpiece according to the embodiment.

FIG. 2A is a schematic diagram showing a configuration of handpiece 70 according to the embodiment. FIG. 2B is a schematic diagram showing an X-Z cross section of handpiece 70 according to the embodiment. Each member in handpiece 70 shown in FIGS. 2A and 2B is housed in optical measurement unit 30 shown in FIG. 1.

As shown in FIGS. 2A and 2B, handpiece 70 includes a projection light generating unit 75, a lens 81, an optical sensor 71, and a prism 72 in a housing 77. In addition to these components, handpiece 70 may include a reflector that reflects light toward object 99, and the like. Lens 81 is held by a movable element of a linear motor described below. For convenience in description, in the embodiment described below, an imaginary straight line indicating a direction in which lens 81 reciprocates linearly is denoted by "L", an axis parallel to straight line L is referred to as "X axis (first axis)", an axis that is perpendicular to straight line L and faces upward on the sheet in FIGS. 2A and 2B is referred to as "Z axis", and an axis perpendicular to each of the X axis and the Z axis is referred to as "Y axis (second axis)".

Projection light generating unit 75 is a laser element, a light emitting diode (LED) or the like serving as a light source. Light from projection light generating unit 75 passes through prism 72 and lens 81 via a projection pattern screen (not shown) arranged in front of projection light generating unit 75 to generate a projection pattern, and is emitted toward object 99 through a reflection unit 66 provided at probe 10, and is reflected by object 99. The light reflected by object 99 passes through lens 81 again via reflection unit 66 and enters prism 72. Prism 72 changes the traveling direction of the light from object 99 to a direction in which optical sensor 71 is located (in this example, a Z-axis direction). The light whose traveling direction has been changed by prism 72 is detected by optical sensor 71. In the example shown in FIG. 2B, the light from projection light generating unit 75 and the light reflected by object 99 and guided to prism 72 are shown separately. However, this is for making the description easier to understand, and actually, handpiece 70 is configured such that both of the lights are guided along the same axis.

When a three-dimensional shape is obtained using the technique of the focusing method, the light having passed through a pattern generating element (not shown) provided between lens 81 and object 99 is projected onto object 99. When lens 81 reciprocates linearly on the same straight line (e.g., straight line L shown in the figure), a focal position of the projection pattern changes. Optical sensor 71 detects the light from object 99 every time the focal position changes. Controller 40 described above computes shape information of object 99 based on the position of lens 81 and a result of detection by optical sensor 71 at that time.

Lens 81 is driven by a first drive unit 80 and reciprocates linearly. When lens 81 reciprocates linearly in the direction of straight line L (X-axis direction), the position of the center of gravity of handpiece 70 is moved by the mass of lens 81, which is transmitted to a hand of a user holding handpiece 70 in the form of vibration. In order to cancel the vibration, handpiece 70 further includes a counterweight 91 in housing 77. Counterweight 91 is driven by a second drive unit 90 and reciprocates linearly in a direction opposite to the direction of linear reciprocation of lens 81.

Counterweight 91 is provided on the rear surface side of projection light generating unit 75 in the X-axis direction so as not to block an optical path between object 99 and lens 81 and an optical path between lens 81 and optical sensor 71.

Specifically, as shown in FIG. 2B, handpiece 70 includes, in housing 77, a first accommodating portion 501 located in a front part of handpiece 70 and a second accommodating portion 502 located in a rear part of handpiece 70. Lens 81 is accommodated in first accommodating portion 501 and counterweight 91 is accommodated in second accommodating portion 502. Furthermore, between first accommodating portion 501 and second accommodating portion 502, handpiece 70 includes a coupling accommodating portion 500 that couples lens 81 accommodated in first accommodating portion 501 to counterweight 91 accommodated in second accommodating portion 502. Optical sensor 71, prism 72 and projection light generating unit 75 described above are accommodated in coupling accommodating portion 500.

Figure 3:
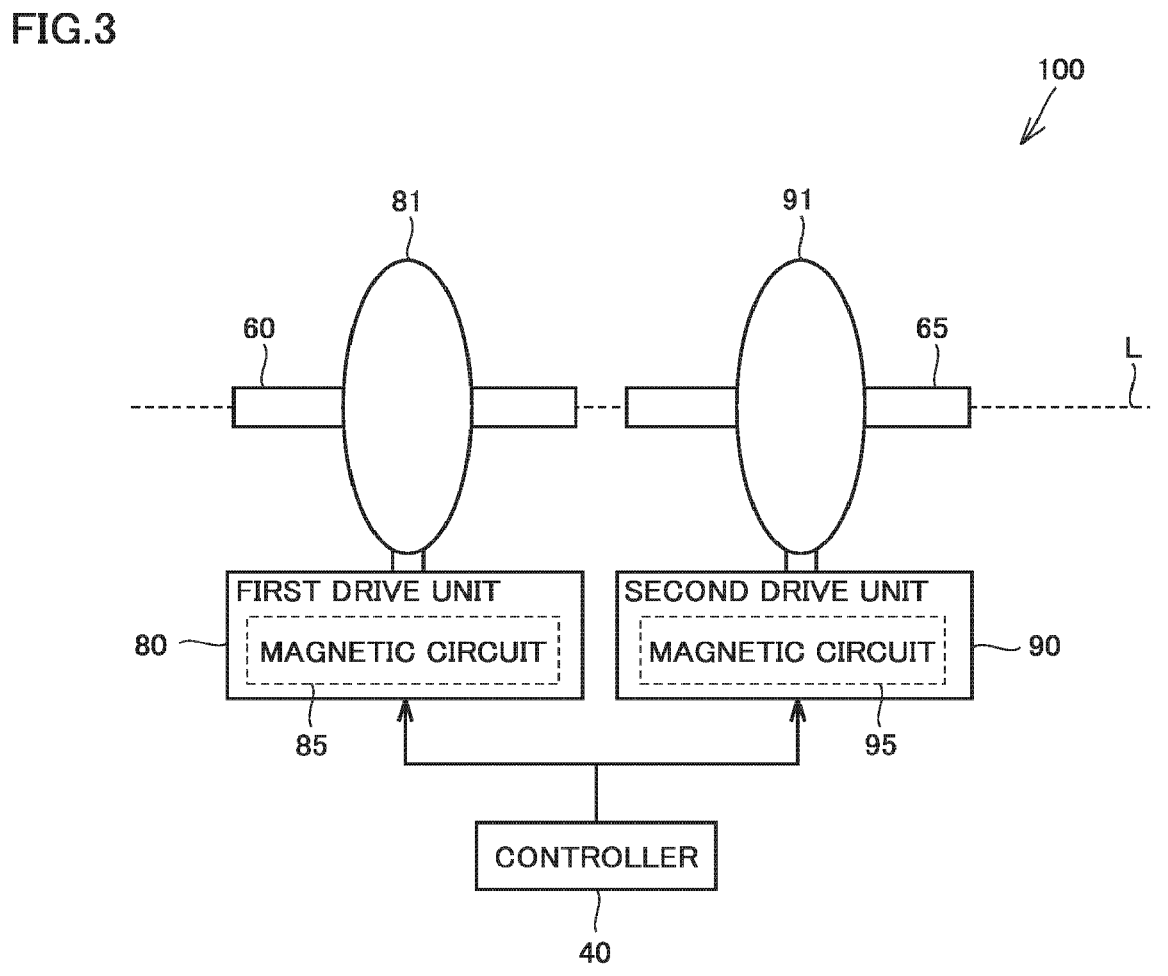

FIG. 3 is a schematic diagram for illustrating a positional relationship between lens 81 and counterweight 91 in three-dimensional scanner 100 according to the embodiment. In the example shown in FIG. 3, housing 77 is omitted. As shown in FIG. 3, lens 81 is supported to reciprocate linearly in the direction of straight line L by a linear guide 60 parallel to straight line L.

Furthermore, first drive unit 80 causes lens 81 held by the movable element to reciprocate linearly in the direction of straight line L by a magnetic circuit 85. In other words, first drive unit 80 is implemented by a linear motor.

Counterweight 91 is a weight provided on straight line L in the linear movement direction of lens 81 and having the same mass as that of lens 81. Counterweight 91 is supported to reciprocate linearly in the direction of straight line L by a linear guide 65 parallel to straight line L. Although linear guide 60 and linear guide 65 are different members in the embodiment, linear guide 60 and linear guide 65 may be formed by an integral member.

Furthermore, second drive unit 90 causes counterweight 91 held by the movable element to reciprocate linearly in the direction of straight line L by a magnetic circuit 95. In other words, second drive unit 90 is implemented by a linear motor.

A specific configuration of each of first drive unit 80 and second drive unit 90 that are linear motors will be described below. Hereinafter, first drive unit 80 and second drive unit 90 will also be collectively simply referred to as "linear motor". Each of first drive unit 80 and second drive unit 90 is controlled by controller 40. Although first drive unit 80 and second drive unit 90 are controlled by common controller 40 in the embodiment, first drive unit 80 and second drive unit 90 may be controlled by different controllers.

When first drive unit 80 causes lens 81 to reciprocate linearly in the direction of straight line L serving as an optical axis, second drive unit 90 causes counterweight 91 to reciprocate linearly by the same distance as that of lens 81 in the direction opposite to the direction of linear reciprocation of lens 81. For example, when lens 81 moves on straight line L by 10 mm in the direction approaching object 99, counterweight 91 moves on straight line L by 10 mm in the direction going away from object 99. When lens 81 moves on straight line L by 15 mm in the direction going away from object 99, counterweight 91 moves on straight line L by 15 mm in the direction approaching object 99.

As described above, counterweight 91 reciprocates linearly by the same distance as that of lens 81 in the direction opposite to the direction of linear reciprocation of lens 81, and thus, the deviation of the center of gravity of handpiece 70 caused by the linear reciprocation of lens 81 can be canceled. As a result, the vibration caused by the linear reciprocation of lens 81 can be canceled by counterweight 91.

[Configuration of Linear Motor]

Figure 4:
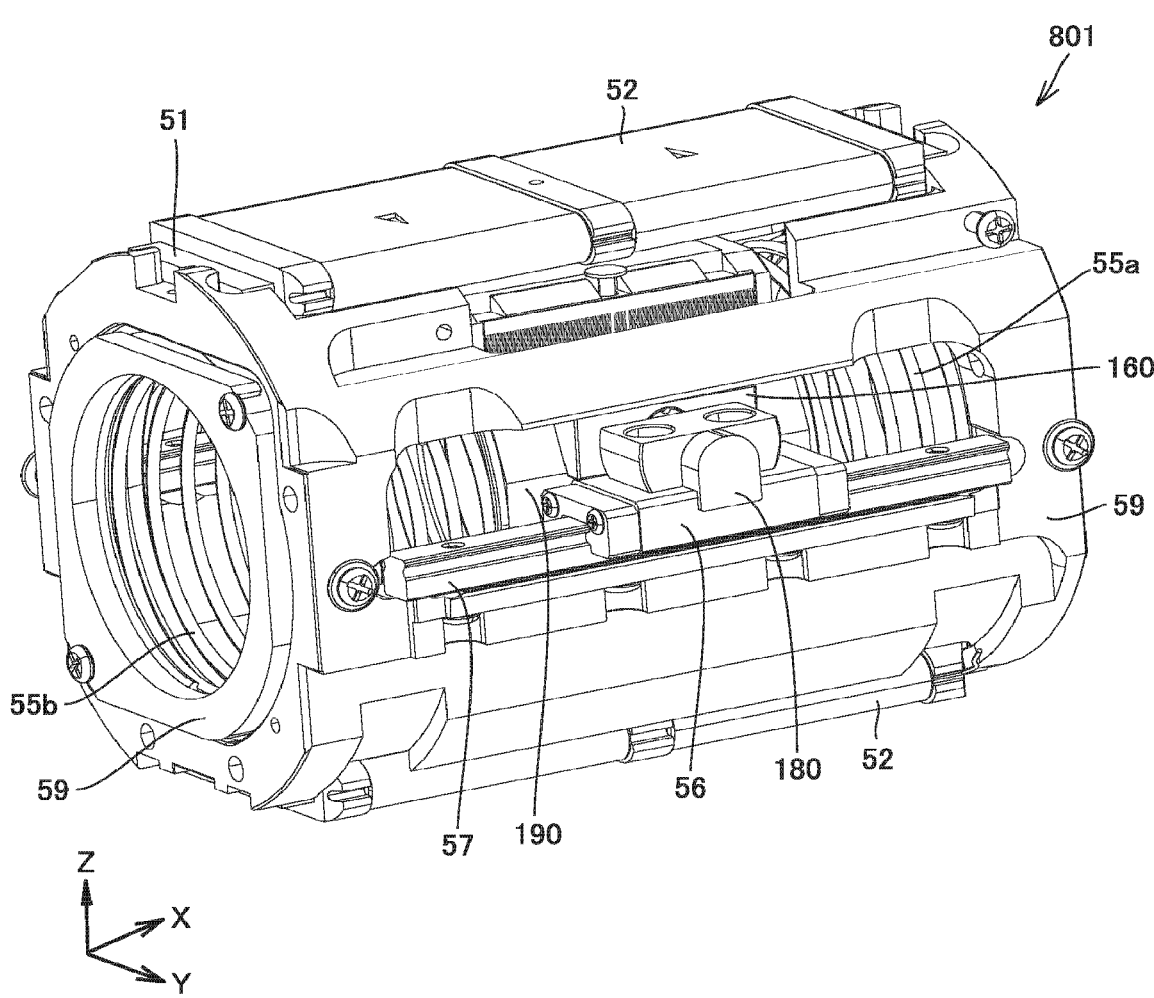
FIG. 4 is a perspective view of a linear motor according to the embodiment.
Figure 5:
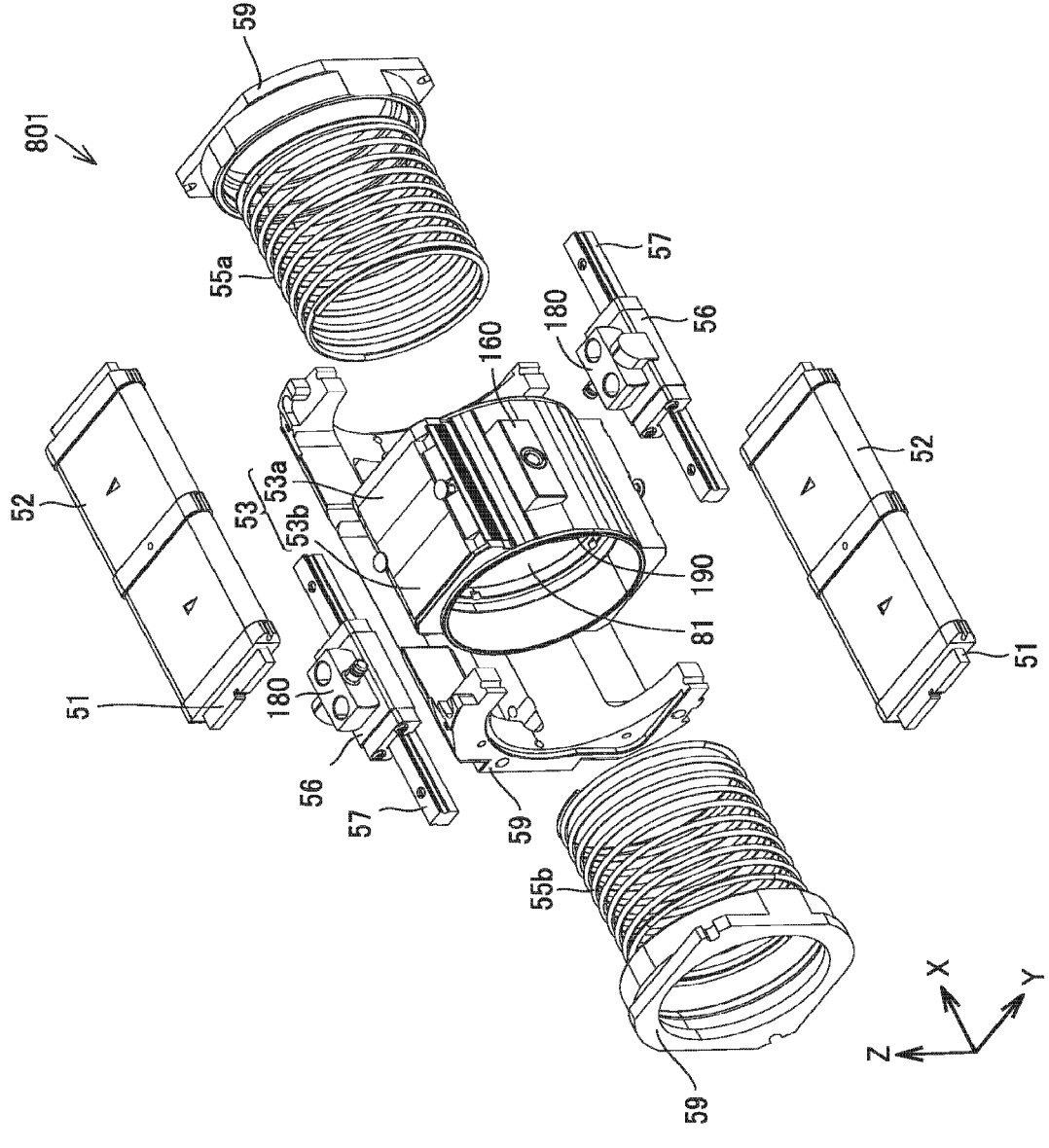
FIG. 5 is an exploded perspective view of the linear motor according to the embodiment.
Figure 6A:
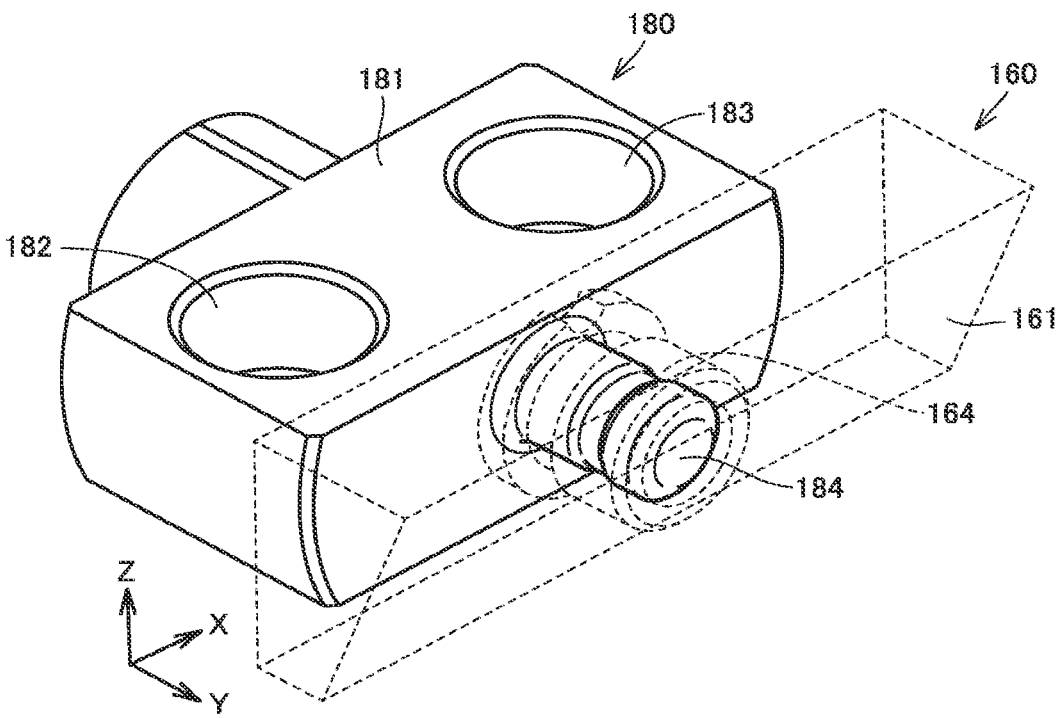
FIG. 6A is a schematic diagram for illustrating fitting between a support portion and a holding portion.
Figure 6B:
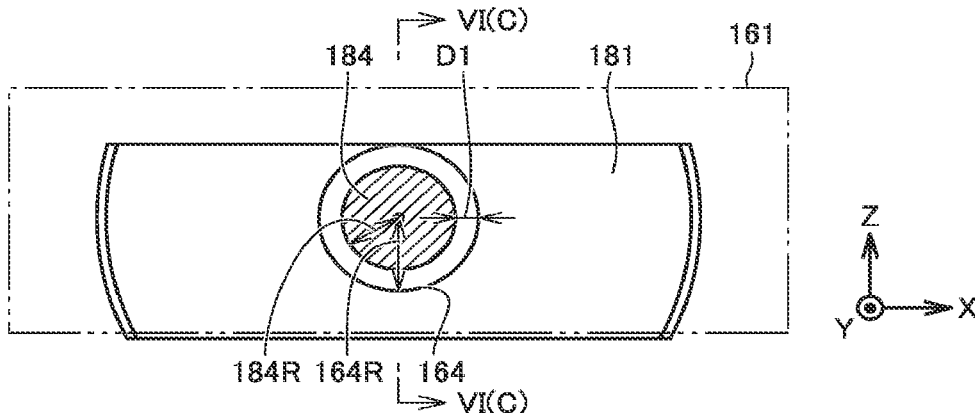
FIG. 6B is a schematic diagram for illustrating play between the support portion and the holding portion.
Figure 6C:
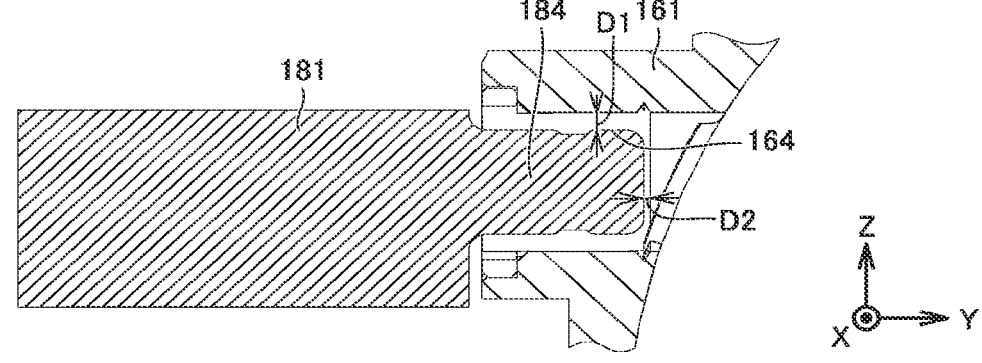
FIG. 6C is a schematic diagram for illustrating play between the support portion and the holding portion.
Figure 7:
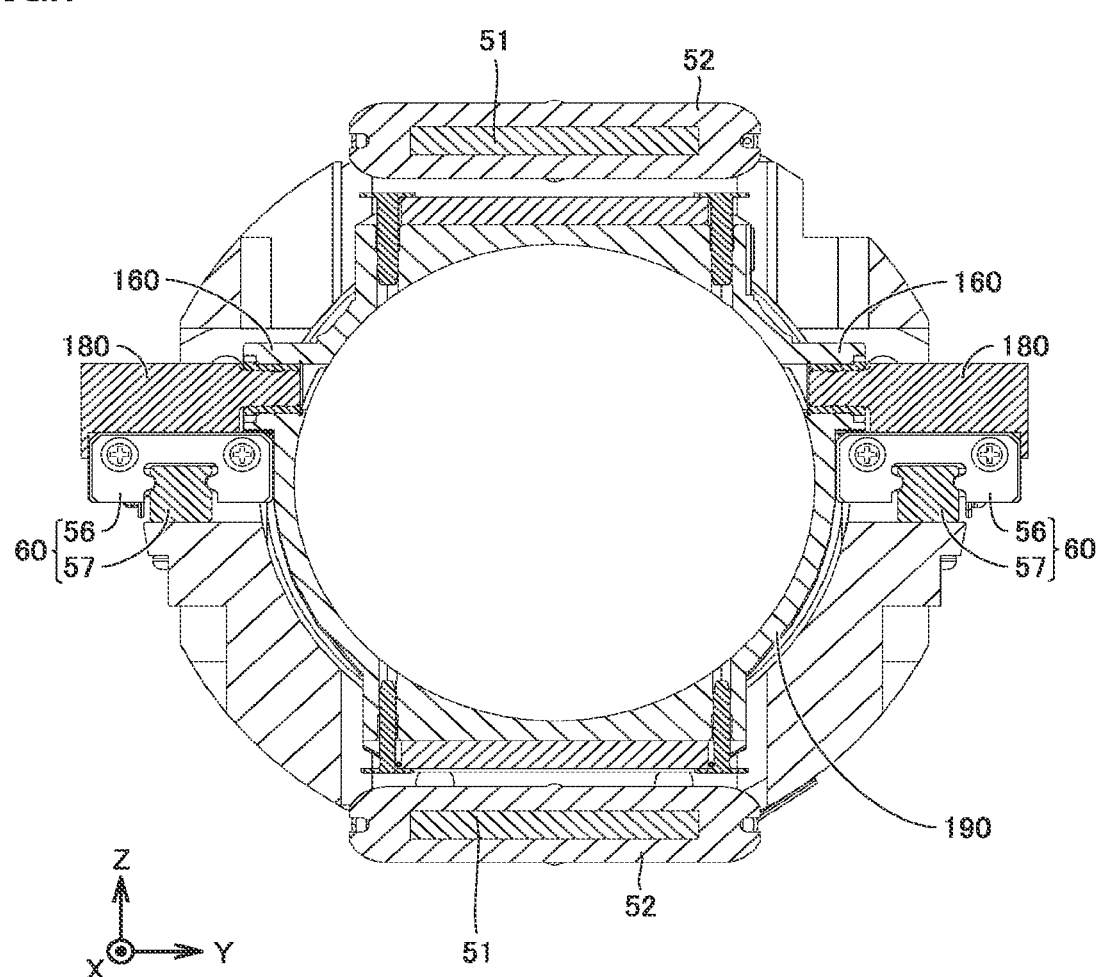
FIG. 7 is a cross-sectional view of the linear motor according to the embodiment taken along an X-Y cross section.

A specific configuration of the linear motor will now be described with reference to the drawings. FIG. 4 is a perspective view of a linear motor 801 according to the embodiment. FIG. 5 is an exploded perspective view of linear motor 801 according to the embodiment. FIG. 6A is a schematic diagram for illustrating fitting between a support portion 180 and a holding portion 160. FIG. 6B is a schematic diagram for illustrating play between support portion 180 and holding portion 160. FIG. 6C is a schematic diagram for illustrating play between support portion 180 and holding portion 160. FIG. 7 is a cross-sectional view of linear motor 801 according to the embodiment taken along an X-Y cross section. Although a configuration of linear motor 801 corresponding to first drive unit 80, of the linear motor, is described in the example shown in FIGS. 4 to 7, a configuration of the linear motor corresponding to second drive unit 90 is similar to the configuration of linear motor 801. Specifically, in the case of the linear motor corresponding to second drive unit 90, lens 81 is replaced with counterweight 91 in the example shown in FIGS. 4 to 7, while the remaining configuration is the same as the configuration of linear motor 801.

Linear motor 801 has magnetic circuit 85 including a yoke 51, a coil 52 and a permanent magnet 53. In addition, linear motor 801 has a movable element 190 that holds lens 81 to surround an outer circumference of lens 81, and permanent magnet 53 is provided on each of the upper side and the lower side of movable element 190 in the figure. Portions of yoke 51 and coil 52 positioned to face permanent magnet 53 constitute a stator of linear motor 801. Permanent magnet 53 is arranged, for example, such that an N pole 53*a* thereof faces in the positive direction of the X axis and an S pole 53*b* thereof faces in the negative direction of the X axis, so as to fix movable element 190.

Since movable element 190 has an opening in the linear movement direction and holds lens 81 (optical component) in the opening, an optical path between object 99 and optical sensor 71 passes through the opening. A spring 55*a* abuts on one end of movable element 190 that holds lens 81, and a spring 55*b* abuts on the other end of movable element 190.

As shown in FIG. 7, in linear motor 801, two linear guides 60, each of which is made up of a rail 57 and a block 56, are provided in parallel with each other on an outer circumferential portion of movable element 190. Two linear guides 60 are arranged at different positions on the outer circumferential side of movable element 190.

More specifically, two linear guides 60 are arranged in parallel with each other at the positions where two linear guides 60 are rotationally symmetrical, with the optical axis (straight line L) that is parallel to the linear movement direction of lens 81 and passes through the center of lens 81 being a rotation axis.

Linear guide 60 includes block 56 and rail 57. Block 56 supports movable element 190 and lens 81 and is fitted onto rail 57, and movement of block 56 in the linear direction along rail 57 causes lens 81 to reciprocate linearly. A viscous lubricant such as grease may be applied to a connection surface between block 56 and rail 57, or the connection surface may be provided with a rolling bearing such as a ball or a roller.

Furthermore, as shown in FIG. 5, spring 55*a* and spring 55*b* are provided to surround the outer circumference of lens 81 so as not to block an optical path in the center portion of lens 81. Each of spring 55*a* and spring 55*b* corresponds to one example of an elastic member. A coil spring or the like is applied as each of spring 55*a* and spring 55*b*. The elastic member is not limited to the spring, but may be any member such as rubber as long as the member is deformed when the force is applied and returns to the original state when the force is removed.

One end of each of spring 55*a* and spring 55*b* abuts on movable element 190 and the other end is fixed by a case 59 of linear motor 801. Furthermore, spring 55*a* and spring 55*b* are held in case 59 such that spring 55*a* and spring 55*b* are allowed to be deformed in the X direction and are difficult to be deformed in the Y-Z direction. Spring 55*a* and spring 55*b* arranged as described above provide the elastic force to movable element 190 in the linear movement direction. In one embodiment, a diameter of each of spring 55*a* and spring 55*b* should be substantially the same as a diameter of lens 81 so as not to block the optical path passing through lens 81.

Lens 81 is supported to be capable of reciprocating linearly by movable element 190 and also by linear guides 60 via support portions 180 and holding portions 160. Specifically, each of holding portions 160 is provided on a part of movable element 190 that holds lens 81. Each of support portions 180 is screwed onto a part of block 56 that moves on rail 57. Support portion 180 and holding portion 160 are fitted.

Fitting between support portion 180 and holding portion 160 will be specifically described with reference to FIGS. 6A to 6C. FIG. 6A is a schematic diagram for illustrating fitting between support portion 180 and holding portion 160. FIG. 6B is a schematic diagram for illustrating play between support portion 180 and holding portion 160. FIG. 6C is a schematic diagram for illustrating play between support portion 180 and holding portion 160.

As shown in FIG. 6A, support portion 180 includes a support portion main body 181, a screw hole 182 and a screw hole 183 formed in support portion main body 181, and a protruding portion 184 protruding from support portion main body 181 to the outside (the holding portion 160 side) in the Y-axis direction. Support portion 180 is screwed onto block 56 through screw hole 182 and screw hole 183. Holding portion 160 includes a holding portion main body 161 and a recessed portion 164 formed in holding portion main body 161. Holding portion 160 is provided on a side surface of movable element 190.

As shown in FIGS. 6B and 6C, protruding portion 184 is a member having such a cylindrical shape that the X-Z cross section has a circular or substantially circular shape and the Y-Z cross section has an elongated rectangular shape in the Y direction. In contrast, recessed portion 164 is a recess (space) having such a cylindrical shape that the X-Z cross section has a circular or substantially circular shape and the Y-Z cross section has an elongated rectangular shape in the Y direction. Protruding portion 184 is configured to be fitted into recessed portion 164. A viscous lubricant such as grease is applied between protruding portion 184 and recessed portion 164.

As described above, support portion 180 screwed on the linear guide 60 side and holding portion 160 provided on the movable element 190 side are fitted, whereby movable element 190 including lens 81 can reciprocate linearly along rail 57.

Recessed portion 164 is greater in a radius of a circle in the X-Z cross section and a length in the Y direction in the Y-Z cross section than protruding portion 184. Specifically, as shown in FIG. 6B, a radius 164R of a circle of recessed portion 164 in the X-Z cross section is greater than a radius 184R of a circle of protruding portion 184 in the X-Z cross section. In addition, FIG. 6C shows a state in which protruding portion 184 is completely fitted into recessed portion 164, and a length 164L of recessed portion 164 in the Y direction in the Y-Z cross section is longer than a length 184L of protruding portion 184 in the Y direction in the Y-Z cross section. Therefore, protruding portion 184 and recessed portion 164 are fitted with play.

For example, in a state in which protruding portion 184 is fitted into recessed portion 164, a difference D1 between radius 164R of recessed portion 164 and radius 184R of protruding portion 184 exists as a clearance in the X-Z cross section, and a difference D2 between length 164L of recessed portion 164 in the Y direction and length 184L of protruding portion 184 in the Y direction exists as a clearance in the Y-Z cross section.

Therefore, even when variations above a certain level occur in radius 184R of protruding portion 184 and radius 164R of recessed portion 164 due to manufacturing variations or the like, assembly errors can be absorbed as long as the variations are within the range of difference D1 such as, for example, 0.01 mm to 0.1 mm, which is a slight gap. In addition, even when variations above a certain level occur in length 184L of protruding portion 184 in the Y direction and length 164L of recessed portion 164 in the Y direction due to manufacturing variations or the like, assembly errors can be absorbed as long as the variations are within the range of difference D2.

Furthermore, play is provided between protruding portion 184 and recessed portion 164 such that difference D2 between length 164L of recessed portion 164 in the Y direction and length 184L of protruding portion 184 in the Y direction is larger than difference D1 between radius 164R of recessed portion 164 and radius 184R of protruding portion 184. Therefore, in a state in which protruding portion 184 is fitted into recessed portion 164, protruding portion 184 is easier to move in the Y direction than in the X direction and in the Z direction.

As described above, between movable element 190 and linear guide 60, support portion 180 provided on the linear guide 60 side and holding portion 160 provided on the movable element 190 side are fitted with play. This can provide an appropriate clearance in fitting between movable element 190 and linear guide 60, and assembly errors can be absorbed. As a result, an influence of assembly errors of three-dimensional scanner 100 on the linear reciprocation of lens 81 can be minimized.

As described above, support portion 180 and holding portion 160 are fitted with play and thereby movable element 190 is attached to linear guide 60. Therefore, the moment of force that occurs around support portion 180 (Y axis) due to the linear reciprocation of lens 81 along linear guide 60 may cause movable element 190 that holds lens 81 to be inclined. Specifically, when movable element 190 moves to the right side in FIG. 3, the counterclockwise moment may occur around support portion 180 and movable element 190 may be inclined such that the right side thereof faces upward. In contrast, when movable element 190 moves to the left side in FIG. 3, the clockwise moment may occur around support portion 180 and movable element 190 may be inclined such that the right side thereof faces downward. In addition, when the operator operates handpiece 70 to provide a load of the external moment around support portion 180 to linear motor 801, movable element 190 may be inclined.

The inclination of movable element 190 varies depending on a driving situation of linear motor 801. Therefore, lens 81 held by movable element 190 is also inclined. In order to correct measurement errors caused by the inclination of lens 81, calibration is performed in three-dimensional scanner 100. However, when the inclination of lens 81 changes depending on the driving situation of linear motor 801, the measurement accuracy may deteriorate.

Figures 8A, 8B:
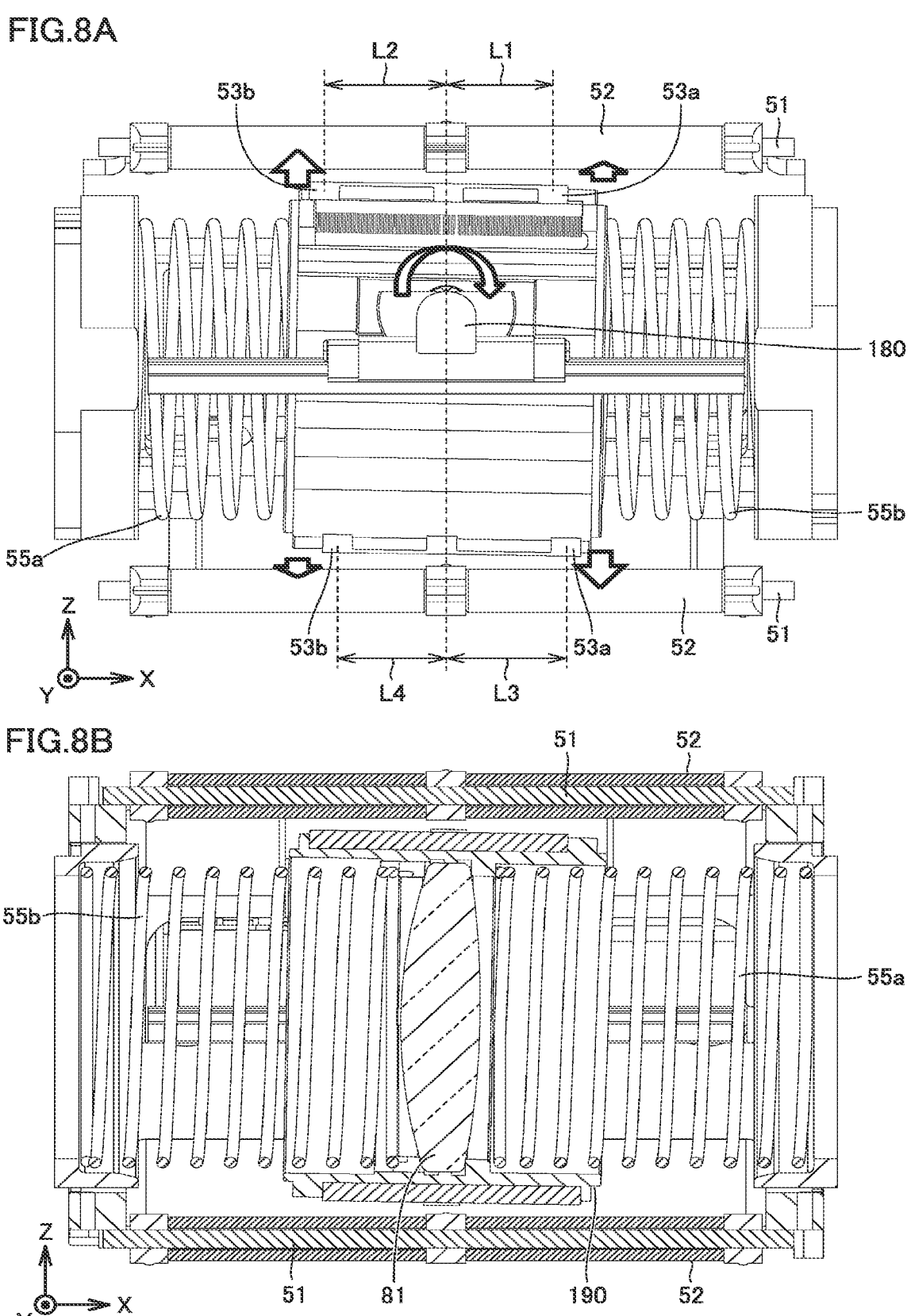
FIGS. 8A and 8B are diagrams for illustrating arrangement of a permanent magnet and inclination of a movable element according to the embodiment.

Thus, linear motor 801 according to the embodiment is configured such that the inclination of movable element 190 does not vary depending on the driving situation. FIGS. 8A and 8B are diagrams for illustrating arrangement of permanent magnet 53 and inclination of movable element 190 according to the embodiment. FIG. 8A shows a side view of linear motor 801 and FIG. 8B shows a cross-sectional view of linear motor 801. As shown in FIG. 8A, in linear motor 801, permanent magnets 53 are attached to movable element 190 at positions where permanent magnets 53 are asymmetrical with respect to holding portions 160. Specifically, upper-side permanent magnet 53 shown in FIG. 8A is arranged such that a distance L2 from each of holding portions 160 to S pole 53b is longer than a distance L1 from each of holding portions 160 to N pole 53a (L1<L2), and lower-side permanent magnet 53 is arranged such that a distance L4 from each of holding portions 160 to S pole 53b is shorter than a distance L3 from each of holding portions 160 to N pole 53a (L4<L3). For example, upper-side permanent magnet 53 is moved by 0.5 mm to the left side in the figure and lower-side permanent magnet 53 is moved by 0.5 mm to the right side in the figure.

Therefore, an imbalance of the magnetic attraction force occurs between permanent magnets 53 and coils 52, and thus, the force that causes S pole 53b to approach coil 52 acts on upper-side permanent magnet 53 at all times, and the force that causes N pole 53a to approach coil 52 acts on lower-side permanent magnet 53 at all times. The size of the arrows shown in FIG. 8A represents the magnitude of the magnetic attraction force. In other words, in linear motor 801, permanent magnets 53 are attached at the positions where permanent magnets 53 are asymmetrical with respect to holding portions 160, whereby the clockwise moment (the moment in the arrow direction shown in FIG. 8A) occurs around support portions 180 and the force that causes movable element 190 to be inclined such that the right side thereof faces downward acts at all times. Therefore, regardless of the driving situation, linear motor 801 is driven with such an inclination that the right side of movable element 190 faces downward at all times.

In three-dimensional scanner 100 in which this linear motor 801 is adopted, the inclination of movable element 190 does not change depending on the driving situation of linear motor 801, and thus, three-dimensional shape data of a tooth and a surrounding soft tissue in an oral cavity can be obtained with a high degree of measurement accuracy if calibration is performed before measurement. In linear motor 801 shown in FIG. 8A, movable element 190 is inclined such that the right side thereof faces downward at all times. However, if permanent magnets 53 are moved in opposite directions, movable element 190 can be inclined such that the left side thereof faces downward at all times. In other words, in linear motor 801, permanent magnets 53 are attached to movable element 190 at the positions where permanent magnets 53 are asymmetrical with respect to holding portions 160, whereby movable element 190 can be stably inclined in the desired direction.

The linear motor that causes counterweight 91 to reciprocate linearly may also be configured similarly to linear motor 801. Although movable element 190 holds lens 81 and thus the inclination of movable element 190 affects the optical axis of lens 81 in linear motor 801, inclination of a movable element does not affect an optical path of measurement in the linear motor that causes counterweight 91 to reciprocate linearly. Therefore, even if the linear motor that causes counterweight 91 to reciprocate linearly is not configured similarly to linear motor 801, the measurement accuracy is not affected.

[Modifications]

The present disclosure is not limited to the above-described embodiment, and various modifications and applications are possible. A modification applicable to the present disclosure will be described below.

The above-described configuration of linear motor 801 is one example, and the number of springs and the locations where the springs are arranged, and further, the number of linear guides and the locations where the linear guides are arranged can be combined as appropriate and designed in consideration of the space in the handpiece. In addition, although linear motor 801 includes two combinations of permanent magnet 53 and coil 52 positioned to face permanent magnet 53 on the upper side and on the lower side of movable element 190 as shown in FIG. 5, linear motor 801 may include any one of these combinations, or may include three or more combinations.

Although support portion 180 having protruding portion 184 protruding toward movable element 190 is provided on the linear guide 60 side and holding portion 160 having recessed portion 164 fitted onto protruding portion 184 is provided on the movable element 190 side in the above-described embodiment, support portion 180 may be provided on the movable element 190 side and holding portion 160 may be provided on the linear guide 60 side. In addition, the shape of each of protruding portion 184 and recessed portion 164 is not limited to the cylindrical shape, but may be any shape. For example, protruding portion 184 may have a spherical shape protruding outward toward the movable element 190 side and recessed portion 164 may have a spherical recess.

Although the three-dimensional scanner is described as one example of the medical care apparatus in the embodiment, the medical care apparatus is also applicable to other uses. Examples of the medical care apparatus include a cutting apparatus that cuts or grinds away an object using a cutting tool (e.g., a scaler tip, a file for root canal treatment, or the like).

Figure 9:
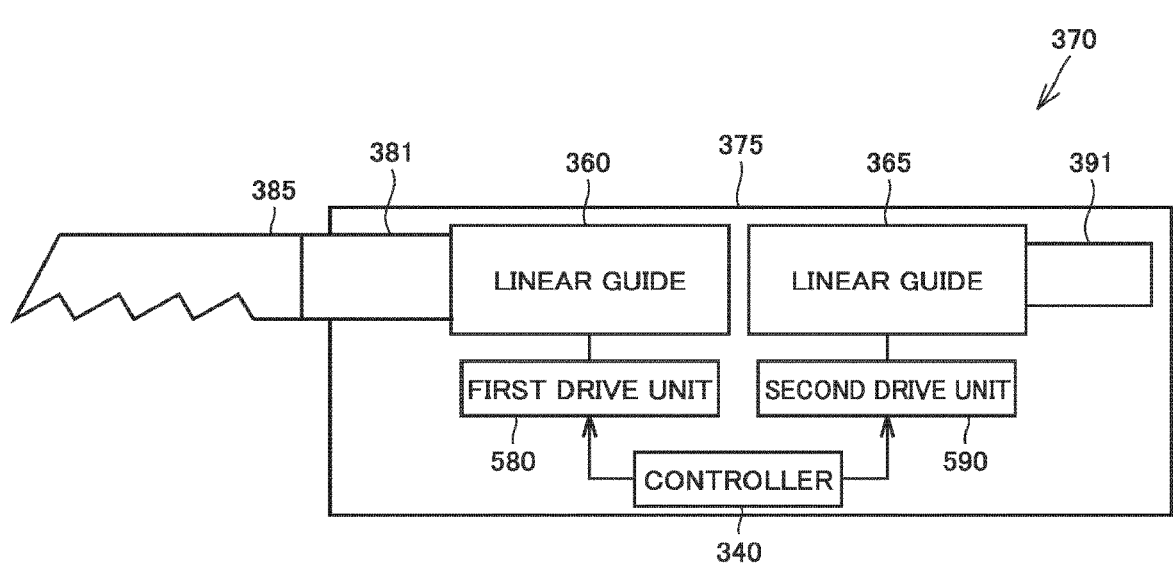
FIG. 9 is a schematic diagram showing a configuration of a cutting apparatus that is a medical care apparatus according to a modification.

FIG. 9 is a schematic diagram showing a configuration of a cutting apparatus 370 that is a medical care apparatus according to a modification. As shown in FIG. 9, cutting apparatus 370 includes a case 375, a cutting tool 385, a cutting holding unit 381 that holds cutting tool 385, a first drive unit 580 that causes cutting holding unit 381 to reciprocate linearly, a counterweight 391 provided on a straight line in a linear movement direction of cutting holding unit 381 and having the same mass as that of cutting holding unit 381, a second drive unit 590 that causes counterweight 391 to reciprocate linearly, a linear guide 360 that guides cutting holding unit 381 such that cutting holding unit 381 reciprocates linearly, a linear guide 365 that guides counterweight 391 such that counterweight 391 reciprocates linearly, and a controller 340 that controls first drive unit 580 and second drive unit 590. Counterweight 391 may have the same mass as a total of the mass of cutting holding unit 381 and the mass of cutting tool 385. Controller 340 controls each of first drive unit 580 and second drive unit 590 such that cutting holding unit 381 and counterweight 391 reciprocate linearly by the same distance in opposite directions.

As described above, in cutting apparatus 370, controller 340 independently controls first drive unit 580 that causes cutting holding unit 381 to reciprocate linearly and second drive unit 590 that causes counterweight 391 to reciprocate linearly, whereby an object (e.g., a tooth) can be cut or ground away using cutting tool 385 held by cutting holding unit 381 and a residual vibration caused by the linear reciprocation of cutting holding unit 381 can be suppressed as much as possible by counterweight 391.

Although controller 340 is housed in case 375 in cutting apparatus 370 shown in FIG. 9, controller 340 may be arranged outside case 375 and connected to first drive unit 580 and second drive unit 590 by a wire as in three-dimensional scanner 100 shown in FIG. 1.

In addition, a medical camera that takes an image of the inside of an oral cavity, the inside of an outer ear, or a digestive organ such as stomach or intestine may be applied as the medical care apparatus. In this case, a lens of the camera may be applied as an object held by the movable element of the linear motor, and a counterweight may be applied as another movable element.

In addition, a microscope may be applied as the medical care apparatus. In this case, a lens in the microscope may be applied as an object held by the movable element of the linear motor, and a counterweight may be applied as another movable element.

Furthermore, a laser pointer that points to an object such as a chart using a laser beam or a laser apparatus that grinds a tooth may be applied as the medical care apparatus. In this case, a lens may be applied as an object held by the movable element of the liner motor, and a counterweight may be applied as another movable element.

It should be understood that the embodiment disclosed herein is illustrative and non-restrictive in every respect. The scope of the present disclosure is defined by the terms of the claims, rather than the description above, and is intended to include any modifications within the scope and meaning equivalent to the terms of the claims. It is to be noted that the configurations exemplified in the embodiment and the configurations exemplified in the modification can be combined as appropriate.

What is claimed is:

1. A linear motor that moves linearly, the linear motor comprising:
   a movable element including a permanent magnet;
   a stator including a coil positioned to face the permanent magnet; and
   two parallel linear guides configured to guide the movable element to move linearly, wherein
   support portions provided on the linear guides, respectively, are fitted with freedom of movement to holding portions provided on the movable element corresponding to the support portions to attach the movable element to the linear guides, and
   a position where the permanent magnet is attached to the movable element is asymmetrical with respect to each of the holding portions.

2. The linear motor according to claim 1, wherein
   each of the support portions is provided on a second axis orthogonal to a first axis parallel to a linear movement direction of the movable element, and
   the movable element has freedom of movement in a direction of rotation about the second axis.

3. The linear motor according to claim 1, wherein
   each of the support portions includes a protruding portion protruding outward toward a movable element side, and
   each of the holding portions includes a recessed portion fitted onto the protruding portion.

4. The linear motor according to claim 3, wherein
   the protruding portion has a cylindrical or spherical shape protruding outward toward the movable element side, and
   the recessed portion has a shape configured to fit onto the protruding portion having the cylindrical or spherical shape.

5. The linear motor according to claim 1, wherein
   a distance from each of the holding portions to a first pole of the permanent magnet is different from a distance from each of the holding portions to a second pole of the permanent magnet.

6. The linear motor according to claim 1, wherein
   the linear motor includes a plurality of combinations of the permanent magnet and the coil positioned to face the permanent magnet.

7. The linear motor according to claim 1, wherein
   the movable element includes an elastic member on at least one surface perpendicular to a linear movement direction.

8. The linear motor according to claim 1, wherein
   the movable element has an opening in a linear movement direction and is configured to hold an optical component in the opening.

9. The linear motor according to claim 1, wherein
   the movable element includes a cutting holding unit configured to hold a cutting tool.

10. A medical care apparatus comprising:
    a linear motor, comprising:
       a movable element including a permanent magnet;
       a stator including a coil positioned to face the permanent magnet; and
       two parallel linear guides configured to guide the movable element to move linearly; and
    a housing configured to hold the linear motor such that the movable element is configured to move linearly along the linear guides, wherein
    support portions provided on the linear guides, respectively, are fitted with freedom of movement to holding portions provided on the movable element corresponding to the support portions to attach the movable element to the linear guides, and a position where the permanent magnet is attached to the movable element is asymmetrical with respect to each of the holding portions.

11. The medical care apparatus according to claim 10, wherein the medical care apparatus is a hand-held three-dimensional scanner.

12. The medical care apparatus according to claim 10, wherein each of the support portions is provided on a second axis orthogonal to a first axis parallel to a linear movement direction of the movable element, and the movable element has freedom of movement in a direction of rotation about the second axis.

13. The medical care apparatus according to claim 10, wherein each of the support portions includes a protruding portion protruding outward toward a movable element side, and each of the holding portions includes a recessed portion fitted onto the protruding portion.

14. The medical care apparatus according to claim 13, wherein the protruding portion has a cylindrical or spherical shape protruding outward toward the movable element side, and the recessed portion has a shape configured to fit onto the protruding portion having the cylindrical or spherical shape.

15. The medical care apparatus according to claim 10, wherein a distance from each of the holding portions to a first pole of the permanent magnet is different from a distance from each of the holding portions to a second pole of the permanent magnet.

16. The medical care apparatus according to claim 10, wherein the linear motor includes a plurality of combinations of the permanent magnet and the coil positioned to face the permanent magnet.

17. The medical care apparatus according to claim 10, wherein the movable element includes an elastic member on at least one surface perpendicular to a linear movement direction.

18. The medical care apparatus according to claim 10, wherein the movable element has an opening in a linear movement direction and is configured to hold an optical component in the opening.

19. The medical care apparatus according to claim 10, wherein the movable element includes a cutting holding unit configured to hold a cutting tool.

20. The linear motor according to claim 3, wherein a length of the protruding portion is less than a length of the recessed portion.

\* \* \* \* \*